US008878838B2

(12) United States Patent
Hautvast

(10) Patent No.: US 8,878,838 B2
(45) Date of Patent: Nov. 4, 2014

(54) VISUALIZING A TIME-VARIANT PARAMETER IN A BIOLOGICAL STRUCTURE

(75) Inventor: Guillaume Leopold Theodorus Frederik Hautvast, Bowen Island (CA)

(73) Assignee: Koninklijke Philips N.V., Eindhoven (NL)

( * ) Notice: Subject to any disclaimer, the term of this patent is extended or adjusted under 35 U.S.C. 154(b) by 466 days.

(21) Appl. No.: 13/146,878

(22) PCT Filed: Jan. 22, 2010

(86) PCT No.: PCT/IB2010/050288
§ 371 (c)(1),
(2), (4) Date: Jul. 28, 2011

(87) PCT Pub. No.: WO2010/086771
PCT Pub. Date: Aug. 5, 2010

(65) Prior Publication Data
US 2011/0285702 A1 Nov. 24, 2011

(30) Foreign Application Priority Data

Jan. 29, 2009 (EP) ..................................... 09151668

(51) Int. Cl.
*G06T 7/20* (2006.01)
*G06T 19/20* (2011.01)
*G06T 15/08* (2011.01)
*G06T 7/00* (2006.01)

(52) U.S. Cl.
CPC ................. *G06T 7/0012* (2013.01); *G06T 7/20* (2013.01); *G06T 19/20* (2013.01); *G06T 2210/41* (2013.01); *G06T 2207/30048* (2013.01); *G06T 15/08* (2013.01); *G06T 2207/10088* (2013.01); *G06T 2219/2012* (2013.01); *G06T 2200/24* (2013.01)

USPC ............................ 345/419; 345/418; 345/600

(58) Field of Classification Search
CPC ................................ G06F 17/00; G06T 15/08
USPC ........................................... 345/418, 419, 600
See application file for complete search history.

(56) References Cited

U.S. PATENT DOCUMENTS

| 5,722,405 A | 3/1998 | Goldberg |
| 5,803,914 A * | 9/1998 | Ryals et al. ................... 600/407 |
| 2005/0124861 A1 | 6/2005 | Breeuwer |

FOREIGN PATENT DOCUMENTS

DE 10331098 A1 2/2005

OTHER PUBLICATIONS

Oeltze S et al: "Integrated Visualization of Morphologic and Perfusion Data for the Analysis of Coronary Artery Disease" Eurographics. IEEE-VGTC Symposium on Visualization, XX, XX, Jan. 1, 2006, pp. 131-138, XP002512740 abstract sections 1, 2.2, 4.1, 4.2, 5.2 figures 1, 4, 8, 9.
Breeuwer M et al: "Analysis of volumetric cardiac CT and MR image data" Medicamundi, Philips Medical Systems, Shelton, CT, US, [Online] vol. 47, No. 2, Aug. 1, 2003, pp. 41-53, XP008103930 ISSN: 0025-7664 Retrieved from the Internet: URL : http ://www.medical.phili pscom/phpwclmain/about/assets/docs/medicamun di/mm_vo147_no2/41-55_breeuwer+anzg_38487. pdf> sections "First-pass myocardial perfusion analysis", "Combination of analysis results" figures 12, 13, 20.
Kuehnel, C. et al. "New Software Assistants for Cardiovascular Diagnosis", Procs Informatik fur den Menschen, 2006—users-www.wineme.fb5.uni-siegen.de. pp. 491-498.
Kuehnel, C. et al. "Enhanced Cardio Vascular Image Analysis by Combined Representation of Results from Dynamic MRI and anatomic CTA", Proc. SPIE/vol. 6918/Cardiac Planning and Guidance, Feb. 2008.
Termeer, M. et al. "CoViCAD: Comprehensive Visualization of Coronary Artery Disease", IEEE Transactions on Visualization and Computer Graphics, vol. 13, No. 6, Nov./Dec. 2007, pp. 1632-1639.
Preim, B. et al. "Survey of the Visual Exploration and Analysis of Perfusion Data", Journal of IEEE Transactions on Visualization and Computer Graphics, 2008, pp. 1-17.

Oeltze, S. "Integrated Visualization of Morphologic and Perfusion Data for the Analysis of Coronary Artery Disease", Eurographics/IEEE-VGTC Symposium on Visualization 2006.

\* cited by examiner

*Primary Examiner* — Phu K Nguyen

(57) ABSTRACT

The invention relates to a system and a method for visualizing a time-variant parameter at a plurality of positions in a biological structure, wherein a visualization display is configured to display a first representation showing a first visualization parameter at a plurality of time intervals, determined in a first volume between a first and a second boundary of the structure, and to display a second representation showing first and second visualization parameters determined in the first and in a second volume extending between the first and the second boundary of the structure. By providing the user with this combination of the two representations, a higher resolution of data may be processed and meaningfully visualized for intermediate volumes between the first and the second boundary. This is based on the insight that it is desirable to view data between boundaries of a structure as well as at different positions through the structure. However, without simple means of visualization, processing a higher resolution of data is not feasible. This is especially useful when performance differences may be present between the structure at the first and the second boundary. For example, perfusion measurements within the myocardium are different for the endocardial and epicardial layers. Therefore, the relative position of the measurements relative to these layers yields valuable data in the evaluation of perfusion. This increases the information which the healthcare professional can extract from imaging data without complicating the representations required to visualize it.

14 Claims, 16 Drawing Sheets

VISUALIZING A TIME-VARIANT PARAMETER IN A BIOLOGICAL STRUCTURE

FIELD OF THE INVENTION

The invention relates to a system and method for visualizing a time-variant parameter in a biological structure.

BACKGROUND OF THE INVENTION

As medical imaging and analysis techniques are continuously improving, the healthcare professional is presented with an ever increasing complexity of the data available for visualization. Starting with measurements of a parameter within a volume of interest, the parameter may be analyzed in different quantitative ways, for example to extract maximum intensity, mean intensity, minimum intensity, average slope values, maximum slope values, minimum slope values, for any desired piece of the volume of interest. The professional must then be able to visualize the data in a meaningful way. For example, visualization of time-intensity curves and associated quantitative analysis data derived from medical images, such as for images of a diseased heart acquired with first pass enhancement cardiac magnetic resonance imaging (MRI).

At present, two-dimensional (2D) visualization techniques are typically used to visualize such time-intensity curves and the associated quantitative analysis data.

For example, a visualization representation known as a perfusogram for a biological structure is known from US application 2005/0124861. Such a perfusogram representation 10 is depicted in FIG. 7—it comprises a 2D array of pixels 15, each pixel having a grey value or color value to represent a mean intensity level. A key 20 is also depicted indicating the mean intensity associated with each grey value or color value. The number of pixels in the horizontal direction 30 is determined by the number of time intervals for which the mean intensity values are determined. The number of pixels in the vertical direction 40 is determined by the number of segments selected for analysis. In other words, the vertical direction provides spatial information, and the horizontal direction provides temporal information.

Such a perfusogram may be visualized in combination with a color overlay on an anatomical gray value image, so that a healthcare professional may relate the spatial information to the anatomy of the patient. It is also known in the art to overlay the anatomical gray value image with color-coded segments, such that the value of a parameter for that segment may be related to the color chosen to depict that segment. For example, as shown in FIG. 6, a color overlay representation 50 comprises an anatomical gray value image 60 of a human heart, overlaid in the region of the myocardium by at least one colored segment 70. The color of the segment 70 is an indication of the mean segment intensity as a measure of perfusion, and a key 80 is also depicted indicating the mean intensity associated with each color.

FIGS. 6 and 7 illustrate the difficulties in presenting complex multidimensional data to the user—FIG. 7 makes it difficult to relate the representation to the actual anatomy of the patient, and FIG. 6 does not show changes in intensity observed over time.

SUMMARY OF THE INVENTION

It is an object of the invention to provide a system for visualizing a time-variant parameter at a plurality of positions.

The invention is defined by the independent claims. Advantageous embodiments are defined in the dependent claims.

According to a first aspect of the invention, a system is provided for visualizing a time-variant parameter at a plurality of positions in a biological structure, the system comprising:

a determination unit configured to determine a value of the time-variant parameter at a plurality of positions in the biological structure, the structure extending in mutually perpendicular X, Y and Z directions; determine the positions of a first and a second boundary extending in the Z direction, and the positions of a first volume extending in Z disposed between the first and the second boundary; determine the positions of a second volume generated by extending the first volume in the X-direction to both the first and the second XY boundary; determine a first visualization parameter for a plurality of time intervals from the time-variant parameters at a plurality of positions in the first volume; determine a second visualization parameter from the time-variant parameters at a plurality of positions in the second volume, and a visualization display configured to display a first representation showing the first visualization parameter at the plurality of time intervals, and display a second representation showing the first and second visualization parameters.

By providing the user with this combination of the two representations, a higher resolution of data may be processed and meaningfully visualized for intermediate volumes between the first and the second boundary. This is based on the insight that it is desirable to view data between boundaries of a structure as well as at different positions through the structure. However, without simple means of visualization, processing a higher resolution of data is not feasible. This is especially useful when performance differences may be present between the structure at the first and the second boundary. For example, perfusion measurements within the myocardium are different for the endocardial and epicardial layers. Therefore, the relative position of the measurements relative to these layers yields valuable data in the evaluation of perfusion. This increases the information which the healthcare professional can extract from imaging data without complicating the representations required to visualize it.

According to a further aspect of the invention, the visualization display is further configured to display a third representation comprising an anatomical gray-value image comprising an XY section through the biological structure, overlaid with the XY section of the first and the second boundary corresponding to the XY section through the structure, and the XY section through the first volume corresponding to the XY section through the structure.

By overlaying, on an anatomical image, the contours representing some of the parameters used in the determination of the representations, the relationship between the representations and the patient's anatomy is further clarified.

According to a further aspect of the invention, the system is further configured to display the first representation comprising a spatial indicator of one of the plurality of first volumes, and a temporal indicator of one of the plurality of time intervals.

In addition or alternatively, the system is configured to display the second representation comprising a spatial indicator of one of the plurality of first volumes.

By providing meaningful indicators to the user, the relationships between the different representations are clarified. This improves the intuitive feel of the displayed information, and makes it easier for the healthcare professional to relate the displayed information to a medical condition.

According to an aspect of the invention, the system further comprises interactive means for a user to determine a parameter in the determination unit or visualization display from the group consisting of: the positions of the first boundary, the positions of the second boundary, the positions of the first volume, the extent of the first volume in XY, the extent of the biological structure in Z, the plurality of time intervals, the first visualization parameter, the second visualization parameter, the XY section through the biological structure and any combination thereof.

By providing high resolution and meaningful data, the system can be made more advantageous and intuitive by allowing the user to directly change parameters used in the determination and visualization of the data.

According to a still further aspect of the invention, the visualization display is further configured to display the second representation using volume rendering.

By introducing the healthcare professional to the possibility of a higher resolution of data analysis for biological structures, a whole new way of data representation becomes possible. Volume rendering techniques, never considered previously for such intermediate volumes in a structure, may be employed to provide even more advantageous representations.

According to an aspect of the invention, a method is provided for visualizing a time-variant parameter at a plurality of positions in a biological structure, comprising determining a value of the time-variant parameter at a plurality of positions in the biological structure, the structure extending in mutually perpendicular X, Y and Z directions; determining the positions of a first and a second boundary extending in the Z direction, and the positions of a first volume extending in Z disposed between the first and second boundaries; determining the positions of a second volume generated by extending the first volume in the X-direction to both the first and the second XY boundary; determining a first visualization parameter for a plurality of time intervals from the time-variant parameters at a plurality of positions in the first volume; determining a second visualization parameter from the time-variant parameters at a plurality of positions in the second volume, and displaying a first representation showing the first visualization parameter at the plurality of time intervals, and displaying a second representation showing the first and second visualization parameters.

According to a further aspect of the invention, the method further comprises displaying a third representation comprising an anatomical gray-value image comprising an XY section through the biological structure, overlaid with the XY section of the first and the second boundary corresponding to the XY section through the structure, and the XY section through the first volume corresponding to the XY section through the structure.

According to an aspect of the invention, a computer program product is provided for carrying out the method of the invention when loaded and run on a computer.

It will be appreciated by those skilled in the art that two or more of the above-mentioned embodiments, implementations, and/or aspects of the invention may be combined in any way deemed useful.

Modifications and variations of the image acquisition apparatus, of the workstation, of the system, and/or of the computer program product, which correspond to the described modifications and variations of the method, can be carried out by a person skilled in the art on the basis of the present description.

A person skilled in the art will appreciate that the system may visualize any form of time-variant multidimensional image data, e.g., to 2-dimensional (2-D), 3-dimensional (3-D) or 4-dimensional (4-D) images, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), and Nuclear Medicine (NM).

The embodiments may also be advantageously combined with the "System For Analyzing Images and Corresponding Method" disclosed in the co-pending application, applicant reference number PH-012697, filed by the same applicant and on the same day as this application. The co-pending application discloses establishing a gradient which is representative of the rate of change in data values between a first and a second border. This gradient may advantageously be used in the embodiments of the current application to determine one of the visualization parameters. Additionally, it may be advantageous to further configure the system of this application to also display the gradientogram disclosed in said co-pending application, or to display the gradientogram in place of the first representation. In particular, the visualization of perfusion in a myocardium may be enhanced by combining the disclosures of the co-pending application with those of the present application.

BRIEF DESCRIPTION OF THE DRAWINGS

These and other aspects of the invention are apparent from and will be elucidated with reference to the embodiments described hereinafter.

In the drawings.

The Figures are purely diagrammatic and not drawn to scale. Particularly for clarity, some dimensions are exaggerated strongly. Similar components in the Figures are denoted by the same reference numerals as much as possible.

DETAILED DESCRIPTION OF THE PREFERRED EMBODIMENTS

Figure 1:
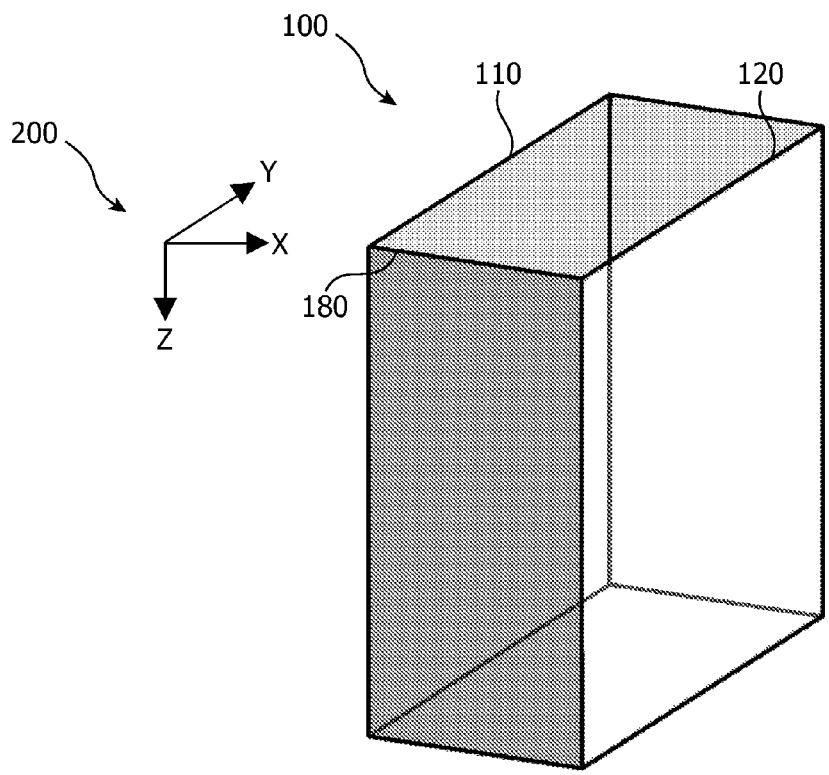
FIG. 1 shows an example of a biological structure for which a representation may be determined.

FIG. 1 depicts a biological structure 100 for which a representation may be determined. The structure 100 extends in mutually perpendicular X, Y and Z directions 200. These directions 200 are chosen arbitrarily—any other coordinate system or convention may be used. The structure 100 is defined by a first boundary 110 and a second boundary 120, each boundary extending in YZ planes. The structure is also bounded by an XY plane 180.

The skilled person will realize that the structure 100 and its boundaries here described do not necessarily coincide with the anatomical extent of biological tissue. For example, the boundaries of the structure 100 may coincide with the walls of a blood vessel or tissue walls, such as the endocardial and epicardial layers of the myocardium, but they may also be selected to define a volume of interest for imaging purposes inside or outside such walls. Similarly, any boundaries in the Z direction may also be arbitrarily selected. Typically, however, the imaging data will have been acquired as slices along XY planes which are digitally assembled. In such a case, the extent in the Z direction may be equal to a selected number of such XY slices.

Note that for the purposes of this invention, the XY slices are assumed to be made at the same time interval.

Figure 2:
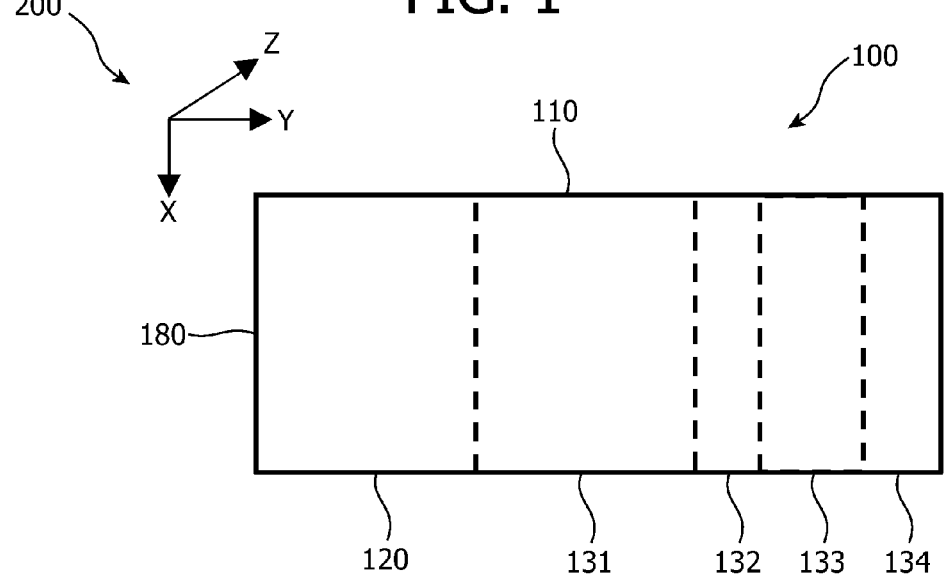
FIG. 2 depicts the biological structure of FIG. 1, viewed along the Z axis, so that the XY plane is closest to the viewer.

FIG. 2 depicts the same structure 100, viewed along the Z axis, so that the XY plane 180 is closest to the viewer. In this example, the first boundary 110 and the second boundary 120 are also depicted, defining the edges of this XY plane 180. One or more pieces of the XY plane 180 are identified as segments 131, 132, 133, 134, which may be of any convenient size and may even be different in size with respect to each other.

Each segment 131, 132, 133, 134 is associated with a segment volume, bounded by the relevant piece of the XY plane 180 and the first boundary 110 and the second boundary 120. For each segment 131, 132, 133, 134, positions in the segment volume are determined, and a parameter associated with each position in the segment volume is analyzed to generate a visualization parameter.

Typically, a series of medical scans are made of such a structure, because the healthcare professional wishes to visualize how the parameter changes in time. This means that a visualization parameter for each segment volume may be determined, and a series of visualization parameters may be determined for each segment volume.

During a first-pass myocardial perfusion examination, the uptake of a contrast agent in the myocardium is monitored dynamically. For example, during a period of 20-40 seconds, 3-5 short axis slices are acquired every 1-2 heart beats, using ECG triggering. The time-intensity curves at individual locations in the myocardium contain important information about local myocardial blood perfusion. Note that for the purposes of this invention, the slices are assumed to be made at the same time interval.

Figure 3:
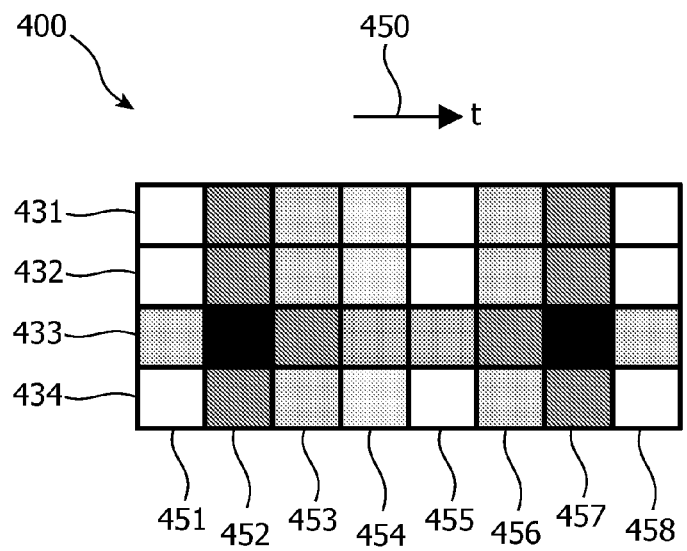
FIG. 3 shows an example of a visualization representation.

An example of a visualization representation 400 is depicted in FIG. 3. The representation 400 comprises a 2D array of pixels, each pixel having a grey value to represent a value of the visualization parameter, for example the higher the value, the whiter the pixel. A color value scheme may also be used. The 2D array has several rows 431, 432, 433, 434 arranged vertically above each other, and several columns 451, 452, 453, 454, 455, 456, 457, 458 arranged horizontally, the rows representing a spatial position and the columns representing a temporal position, in other words moments in time. An arrow 450 indicates the progression of the time interval, from left to right. Each row 431, 432, 433, 434 represents the change in the visualization parameter for each segment volume associated with the segments 131, 132, 133, 134, respectively, over a number of time intervals 451, 452, 453, 454, 455, 456, 457, 458. The time intervals 451, 452, 453, 454, 455, 456, 457, 458 represented may comprise all the acquired time series of data, or an arbitrary selection.

Figure 7:
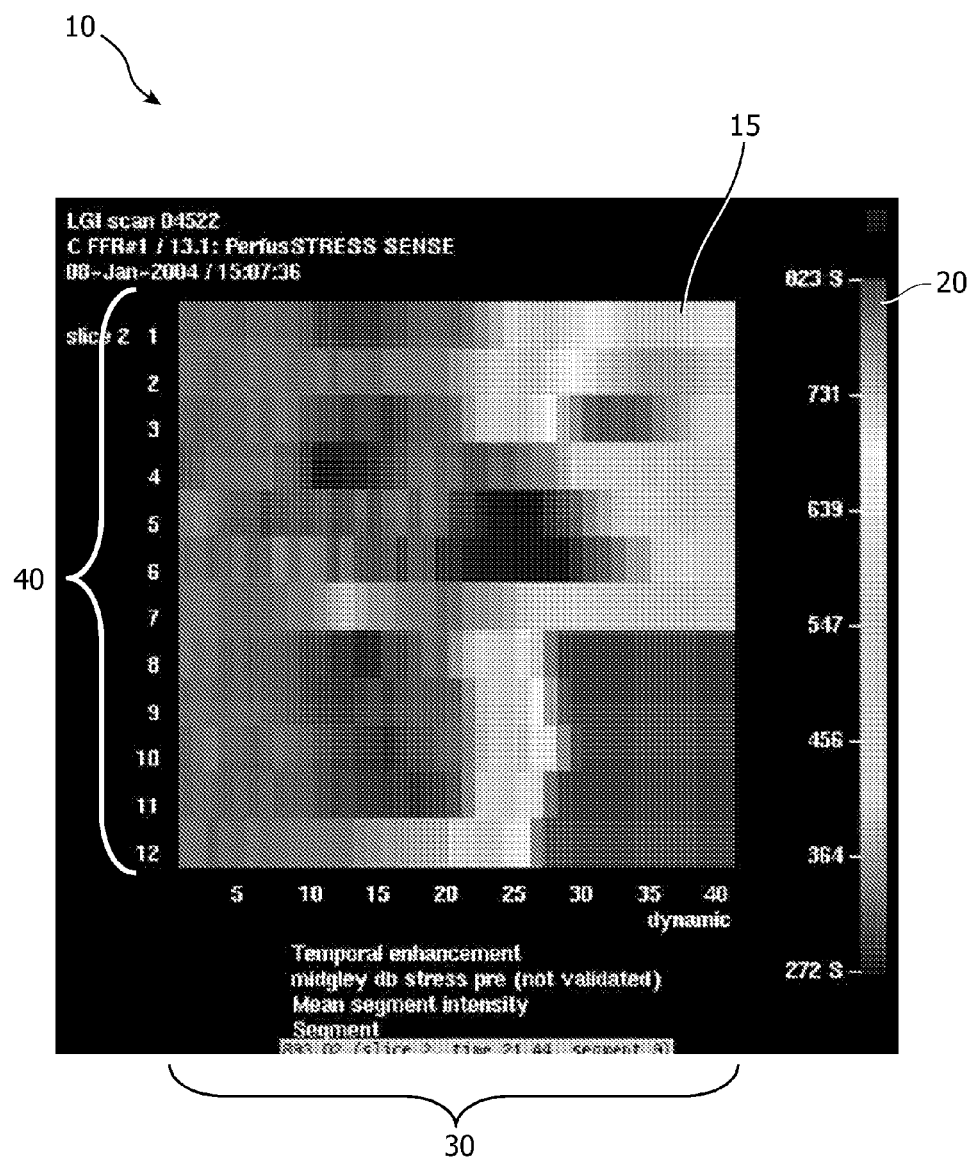
FIG. 7 depicts an example of a perfusogram representation.

For example, if the parameter associated with each position is an intensity measured during a medical scan, then the visualization parameter may be the mean segment intensity. If the intensity is a measure of, for example, perfusion, then the visualization parameters may be visually represented to the user as a perfusogram, which is a specific example of the representation 400 depicted in FIG. 3. An example of a perfusogram representation is illustrated in FIG. 7, as explained above.

Figure 16:
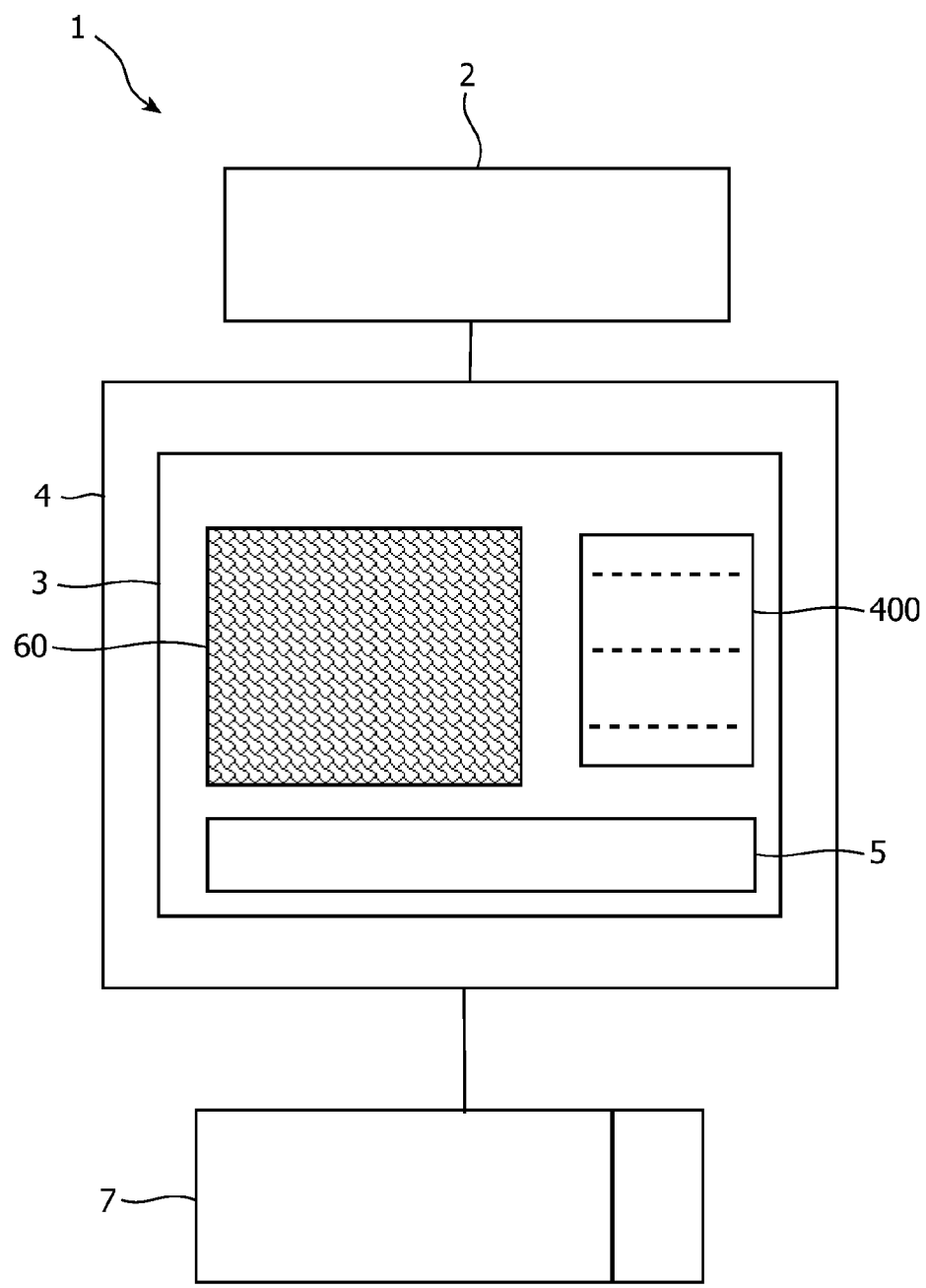
FIG. 16 shows a system for visualizing a time-variant parameter.

Producing such a representation 400 to visualize a time-variant parameter at a plurality of positions in a biological structure 100 may be performed by a suitable system. An example of such a system 1 is depicted in FIG. 16. The system comprises a determination unit 2 and a visualization display 3. The determination unit 2 is configured to determine a value of the time-variant parameter at a plurality of positions in the biological structure 100, and to determine the positions of a first boundary 110 and a second boundary 120 extending in the Z direction, and the positions of a segment volume, associated with a segment 131, 132, 133, 134, extending in Z disposed between the first 110 and the second 120 boundary, and to determine the visualization parameter for a plurality of time intervals 451, 452, 453, 454, 455, 456, 457, 458 from the time-variant parameters at a plurality of positions in the segment volumes. The visualization display 3 is configured to display a representation 400 showing the visualization parameter at a plurality of time intervals 451, 452, 453, 454, 455, 456, 457, 458.

Typically, the user is provided with a means 7 to interact with the system, so that the user may influence what is displayed. A user may use a workstation 4 to perform these interactions, for example during image acquisition, image viewing, image analysis and image modification. The workstation 4 comprises the visualization display 3 for displaying one or more representations 400, and typically for displaying anatomical gray value image 60. The user interactions may be provided in one or more forms, such as icons, thumbnails, menus, and pull-down menus. The workstation 4 also comprises a means 7 for the user to interact with the workstation 4, which may comprise a keyboard, mouse, trackball, pointer, drawing tablet.

Figure 4:
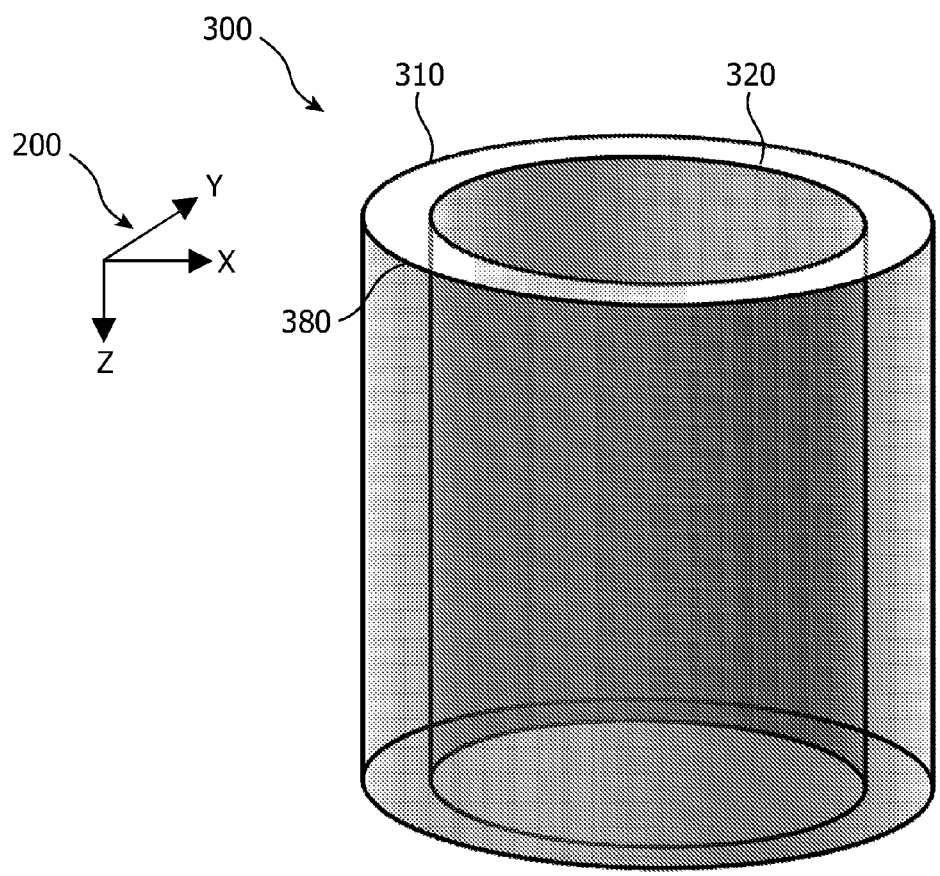
FIG. 4 depicts a second example of a biological structure for which a representation may be determined.

The biological sample 100 in FIGS. 1 and 2 approximates a rectangular volume. However, the same representation may be used for any structure which approximates a 3D geometric figure with approximately parallel congruent bases having approximately the same orientation. FIG. 4 depicts a biological structure 300 which approximates a hollow cylinder volume. The structure 300 extends in mutually perpendicular X, Y and Z directions 200. Again, these directions 200 are chosen arbitrarily—any other coordinate system or convention may be used. In particular, a radial coordinate system may also be advantageous for such a structure. The structure 300 is defined by a first boundary 310 and a second boundary 320, each boundary extending in the Z planes. The structure is also bounded by an XY plane 380.

Figure 5:
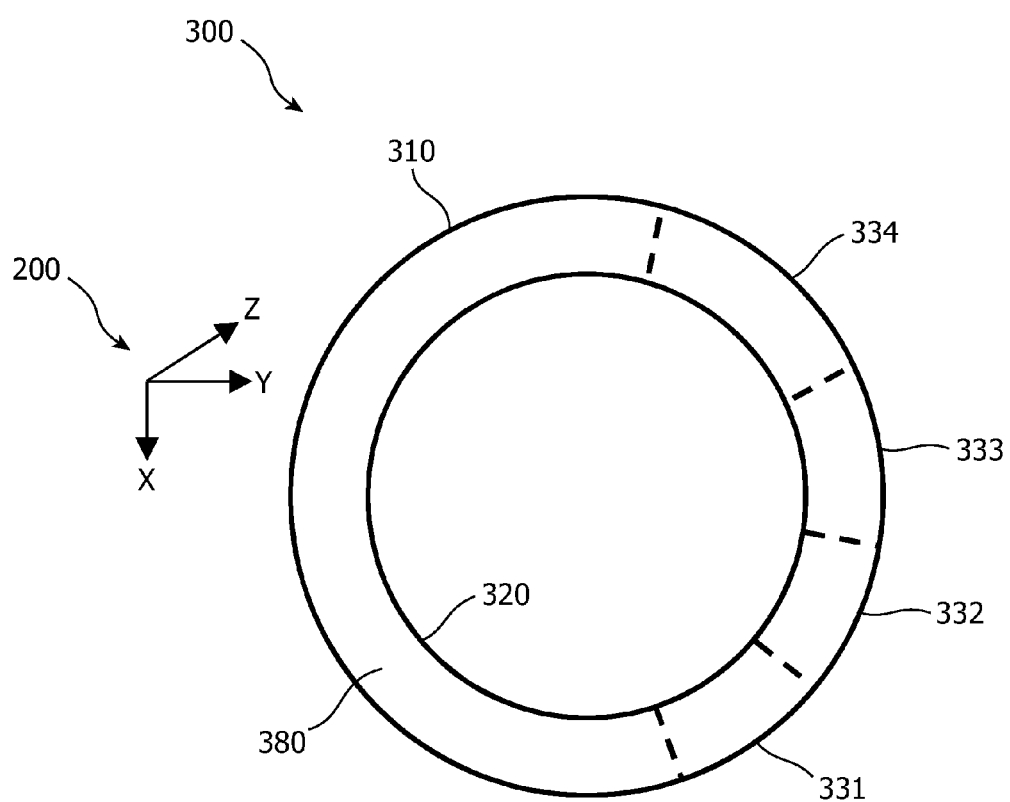
FIG. 5 depicts the biological structure example of FIG. 4, viewed along the Z axis, so that the XY plane is closest to the viewer.
Figure 6:
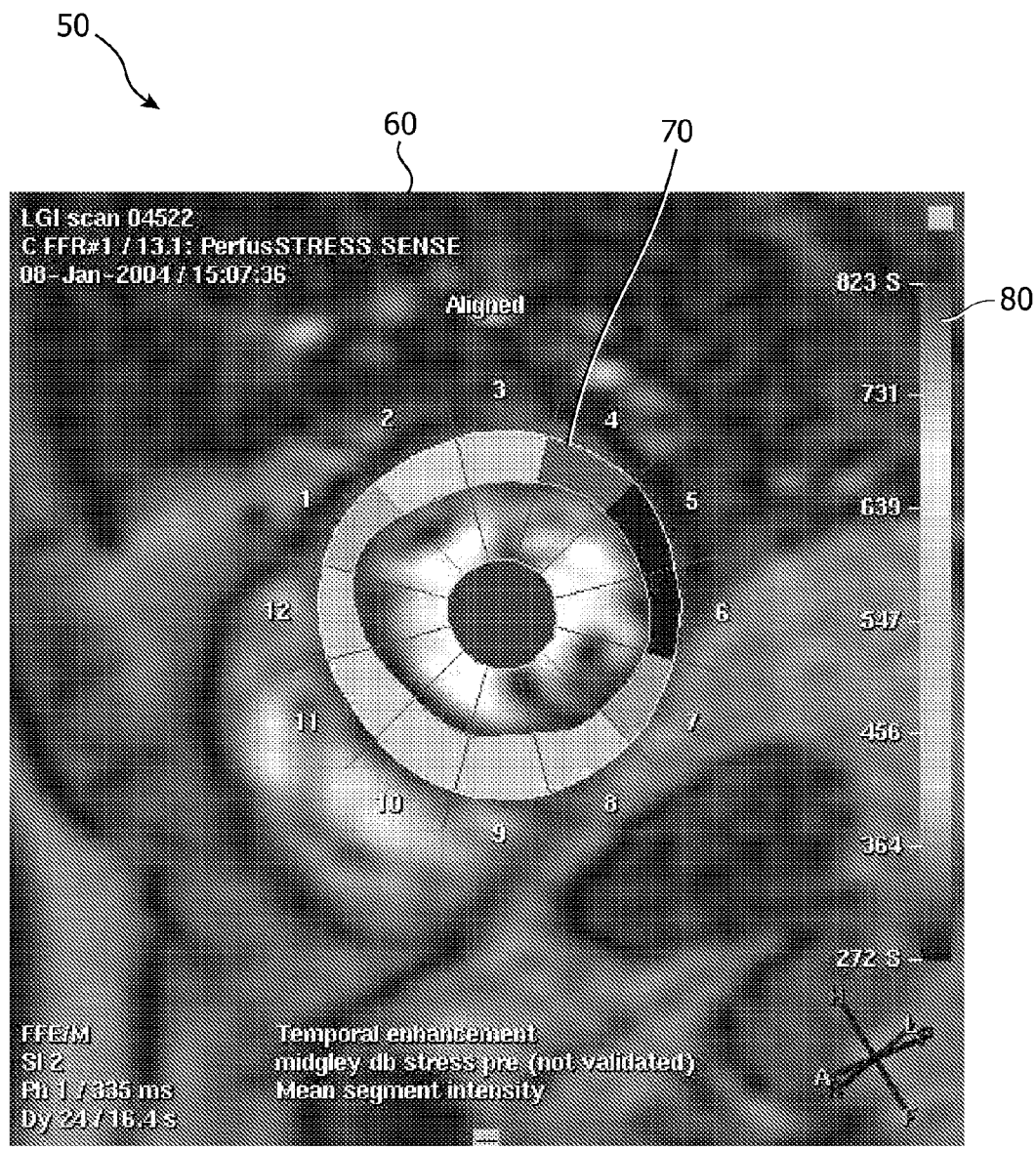
FIG. 6 shows an example of a color overlay representation.

FIG. 5 depicts the same structure 300, viewed along the Z axis, so that the XY plane 380 is closest to the viewer. In this example, the first boundary 310 and the second boundary 320 are also depicted, defining the edges of this XY plane 380. One or more pieces of the XY plane 380 are identified as segments 331, 332, 333, 334. The number of segments chosen and their sizes is arbitrary, chosen depending on the biological structure 300 and the type of analysis desired.

Each segment 331, 332, 333, 334 is associated with a segment volume, bounded by the relevant piece of the XY plane 380 and the first boundary 310 and second boundary 320. For each segment 331, 332, 333, 334, positions in the segment volume are determined, and a parameter associated with each position in the segment volume is analyzed to generate a visualization parameter.

If a series of medical scans are made of such a structure, a visualization parameter for each segment volume may be determined, and a temporal, or time-variant, series of visualization parameters may be determined for each segment volume. This may also be visually displayed to the healthcare professional as the representation 400 depicted in FIG. 3. In this case, each row 431, 432, 433, 434 represents the change in the visualization parameter of the segment volume associated with segments 331, 332, 333, 334, respectively, over a number of time intervals 451, 452, 453, 454, 455, 456, 457, 458.

It will be apparent to the skilled person that small sections of the cylindrical structure 300 may approximate a rectangular volume 100 as depicted in FIG. 1, enabling this technique to be used for many types and shapes of biological structure.

For example, the structure may be one or more sections of a human myocardium for which the degree of perfusion is to be measured. The most frequently occurring heart disease is ischemia due to the (partial) occlusion of a coronary artery. First pass enhancement cardiac MRI may be used to assess the severity of perfusion deficits caused by coronary artery occlusions, by studying the uptake of contrast agent in the myocardial tissue after the first pass of a contrast bolus. This procedure is often performed on patients at rest and under stress (using pharmacological agents to increase the heart rate) as perfusion deficits are often stress induced. The myocardium may be conveniently divided into segments, such as those depicted in FIGS. 2 and 5, for performing the perfusion determination and for visualization of the results, using the representation of FIG. 3.

It may be advantageous to provide the healthcare professional with representations of layers within a biological structure 100, 300, instead of segment volumes. Using the segments 131, 132, 133, 134 in FIG. 1 and the segments 331, 332, 333, 334 in FIG. 5, the user is limited to the selection of particular segments. This limits the resolution which can be visualized. However, if the determination is modified so as to provide the visualization of layers between the first boundary 110, 310 and the second boundary 120, 320, the user is given additional freedom to examine the biological structure.

Figure 8A:
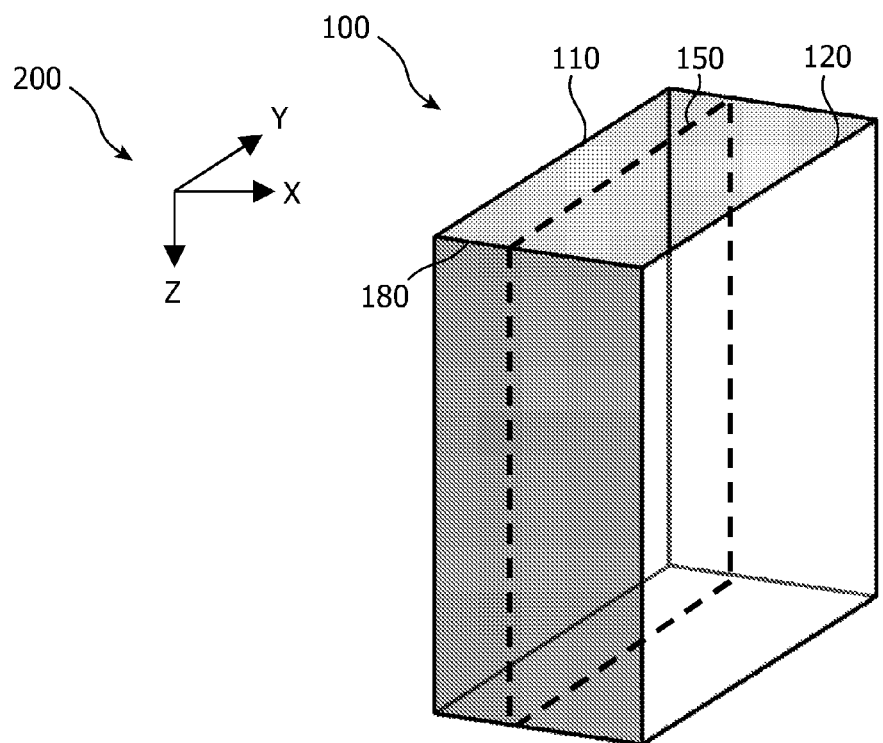
FIG. 8 depicts the biological structure of FIG. 1 and the different volumes which may be defined.

FIG. 8A depicts the biological structure 100 of FIG. 1 for which a representation may be determined. It may be advantageous in some applications to provide an extra degree of freedom by determining the time-variant parameter within the biological structure 100 for an intermediate layer 150 situated between the first boundary 110 and the second boundary 120.

For example, if the biological structure is the myocardium, the first boundary 110 may represent the epicardial (or outer) layers and the second boundary 120 may represent the endocardial (or inner) layers. When determining perfusion, it may be advantageous to visualize layers at different positions between the endocardial and epicardial layers, because it is known, from physiology, that the endocardium shows a higher rest perfusion, but is more susceptible to ischaemia than the epicardium. As such, visualizations of perfusion in different layers of the myocardial wall provide for accurate diagnosis and staging of ischemic heart disease.

Determining parameter values for such a layer 150 requires a high resolution of differentiation between the different tissues found between the inner boundary 120 and outer boundary 110 of the biological structure 100. Correspondingly, increasing the spatial resolution of the determination increases the number of data points which must be visualized. This greatly complicates the interaction with the user because there are more choices available, and more information must be displayed to the user at the same time.

Figure 8B:
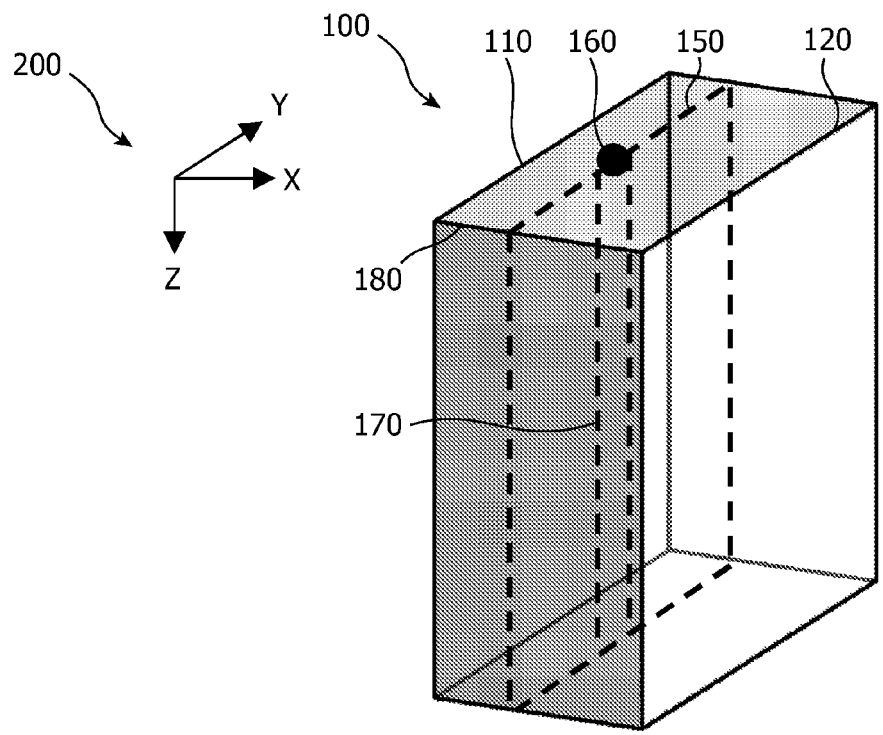

FIG. 8B depicts the same structure 100, wherein a point 160 on the layer 150 has been selected, which the user wishes to see visualized. The point 160 may be considered a piece in the XY plane 180 which is smaller in the X direction than the distance between the first boundary 110 and the second boundary 120. Any convenient size and shape of point 160 may be used, balancing the need between higher resolution and faster processing. Typically, the point 160 will have a minimum size of 1 voxel. The point 160 is associated with a first volume 170, extending in the Z direction at a position between the inner boundary 110 and the outer boundary 120, in other words a section of the intermediate layer 150 extending in both the Y and Z directions. For the first volume, positions in the volume are determined, and a parameter associated with each position in the volume is analyzed to generate a first visualization parameter for a plurality of time intervals.

Figure 8C:
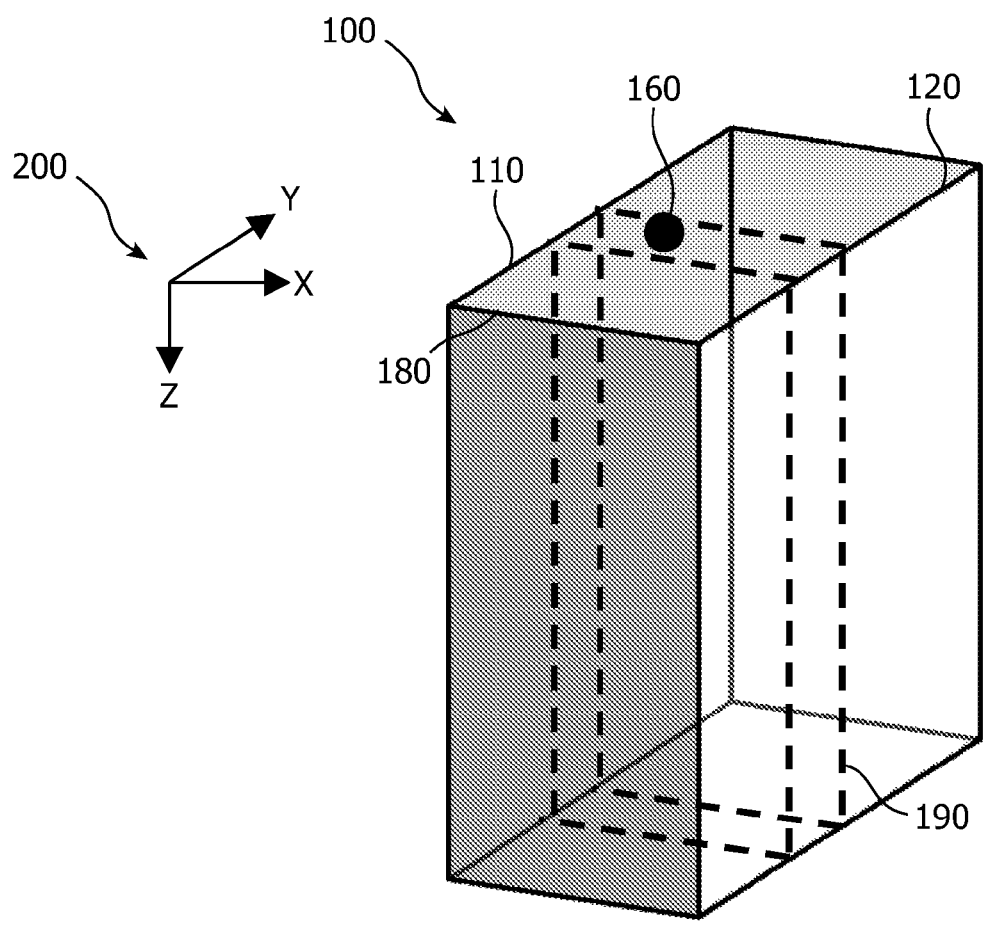

FIG. 8C depicts the same structure 100, wherein a second volume 190 is generated by extending the first volume until it intersects both the first boundary 110 and the second boundary 120. The positions in the second volume are determined, and a parameter associated with each position in the second volume is analyzed to generate a second visualization parameter for one of the plurality of time intervals.

Figure 9A:
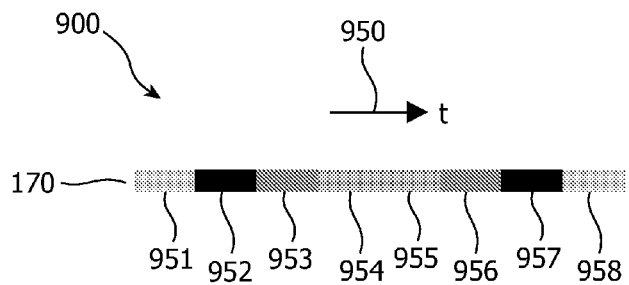
FIG. 9 depicts examples of data representations.

FIG. 9A depicts, in a representation 900, one row 170 of the first visualization parameter at several periods in time 950, namely at intervals 951, 952, 953, 954, 955, 956, 957, 958. This Figure shows the user the change with respect to time of the visualization parameter in the first volume, disposed between the first boundary 110 and the second boundary 120.

Figure 9B:
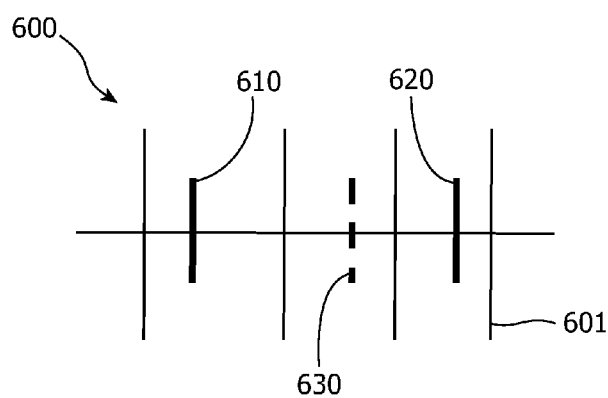

FIG. 9B is a representation 600 of the relationship at a selected time interval, being one of the plurality of time periods, between the first visualization parameter 630 determined at said selected time interval, and a second visualization parameter 610, derived from the data analysis of the second volume. Optionally, a grid 601 may be provided to indicate the scale. For example, the second visualization parameter 610 may represent the maximum value of the first visualization parameter determined in the second volume 190. This is particularly advantageous in cases where each parameter visualized can be referenced to the same scale, preferably having the same unit of measure.

The second visualization parameter 610 may also represent the value of the first visualization parameter at a particular position in the second volume 190 between the first boundary 110 and the second boundary 120. For example, if perfusion in the myocardium is measured, the intensity for the epicardial layer or the intensity for the endocardial layer may be selected as a suitable second visualization parameter 610.

It may also be advantageous to determine a plurality of visualization parameters from the positions in the second volume 190, for example the value of the first visualization parameter at both the first boundary 110 and the second boundary 120 to visualize a second 610 and a third 620 visualisation parameter, respectively. For example, if perfusion in the myocardium is measured, the intensity for the epicardial layer may be used for the second visualization parameter 610 and the intensity for the endocardial layer may be used for the third visualization parameter 620.

Other possible quantitative analysis techniques that may be used to determine visualization parameters include upslope, deconvolution, and Patlak. Additionally, the skilled person will realize that such techniques may be combined with arithmetical and statistical operations, such as averaging or weighting, to provide a suitable and meaningful representation.

Figure 10:
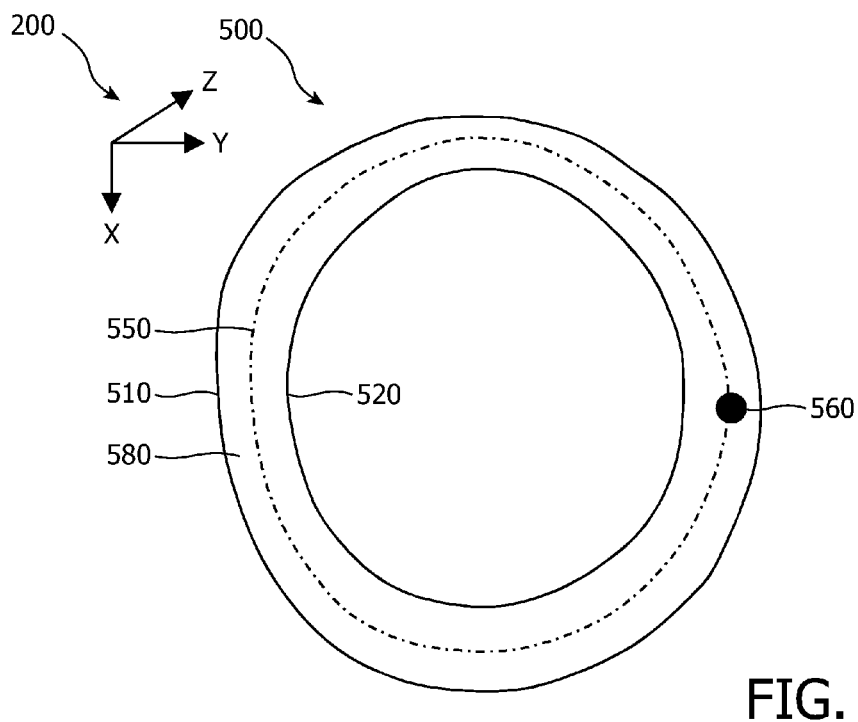
FIG. 10 depicts a biological structure which approximates a hollow cylinder volume.

As described above, a similar determination may be performed with any structure which approximates a 3D geometric figure with approximately parallel congruent bases having approximately the same orientation. FIG. 10 depicts a biological structure 500 which approximates a hollow cylinder volume. The structure 200 is viewed along the Z axis, so that the XY plane 580 is closest to the viewer. In this example, the first boundary 510 and the second boundary 520 are also depicted, defining the edges of this XY plane 580.

On the layer 550 a point 560 has been selected which the user wishes to see visualized. The point 560 may be considered a piece in the XY plane 580, which piece is smaller than the distance between the first boundary 510 and the second boundary 520. Any convenient size and shape of point 560 may be used, balancing the need between higher resolution and faster processing. Typically, the point 560 will have a minimum size of 1 voxel. The point 560 is associated with a first volume, extending in the Z direction at a position between the inner boundary 510 and the outer boundary 520. For the first volume, the positions in the volume are determined, and a parameter associated with each position in the volume is analyzed to generate a first visualization parameter for a plurality of time intervals. A second volume is generated by extending the first volume until it intersects both the first boundary 510 and the second boundary 520. For the second volume, the positions in the second volume are determined, and a parameter associated with each position in the second volume is analyzed to generate a second visualization parameter for one of the plurality of time intervals.

Figure 11A:
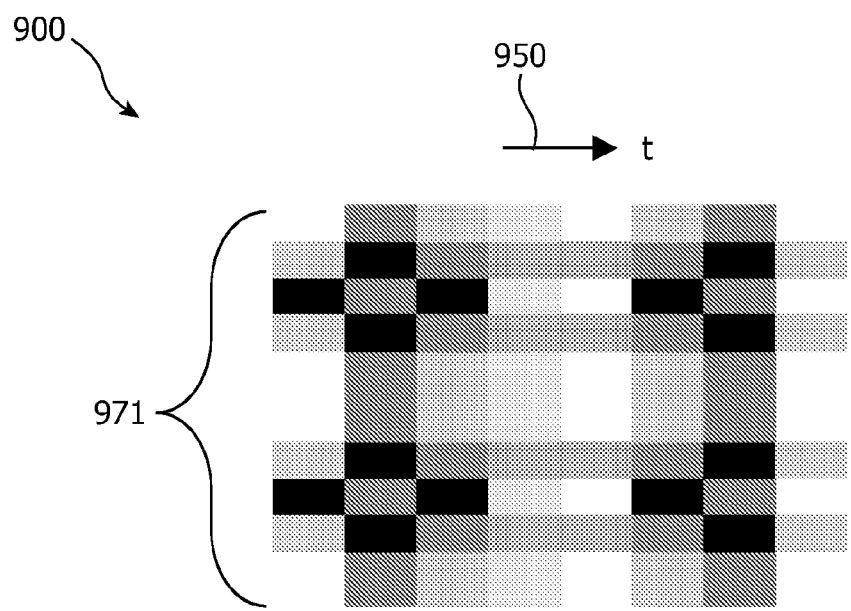
FIG. 11 depicts further examples of data representation.

FIG. 11A depicts a representation 900 similar to the one depicted in FIG. 9A, with this difference that the representation 900 shown here comprises a plurality of rows 971 of the first visualization parameter at several periods in time 950. Each row 971 displays the first visualization parameters for a particular spot position 560 along the intermediate layer 550. This shows the user the change in the time-variant parameter in the first volume, disposed between the first boundary 510 and the second boundary 520.

Figure 11B:
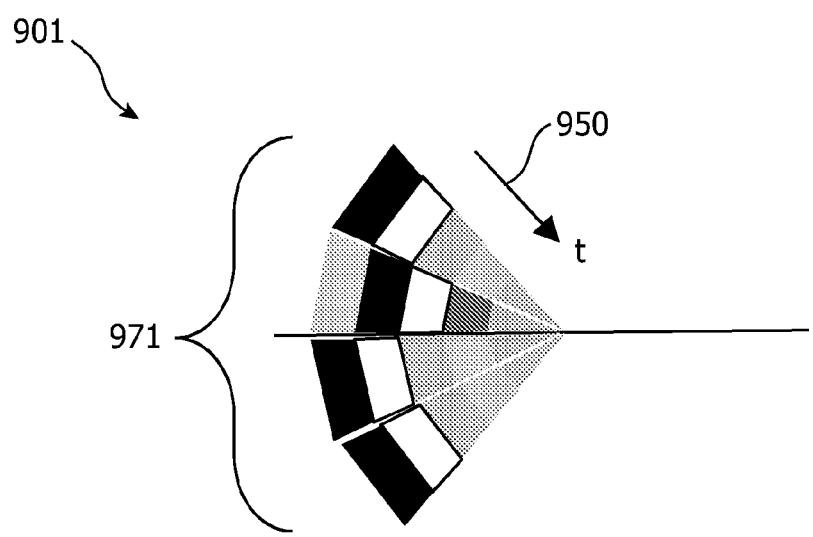

FIG. 11B depicts representation 901, which is an alternative to representation 900. Here the representation 901 comprises a plurality of circular segments 971 of the first visualization parameter at several periods in time 950. Each segment 971 displays the first visualization parameters for a particular spot position 560 along the intermediate layer 550. This shows the user the change in the time-variant parameter in the first volume, disposed between the first boundary 510 and the second boundary 520. Such a circular representation may be advantageous if the biological structure 300 is also approximately circular in cross-section.

Figure 12:
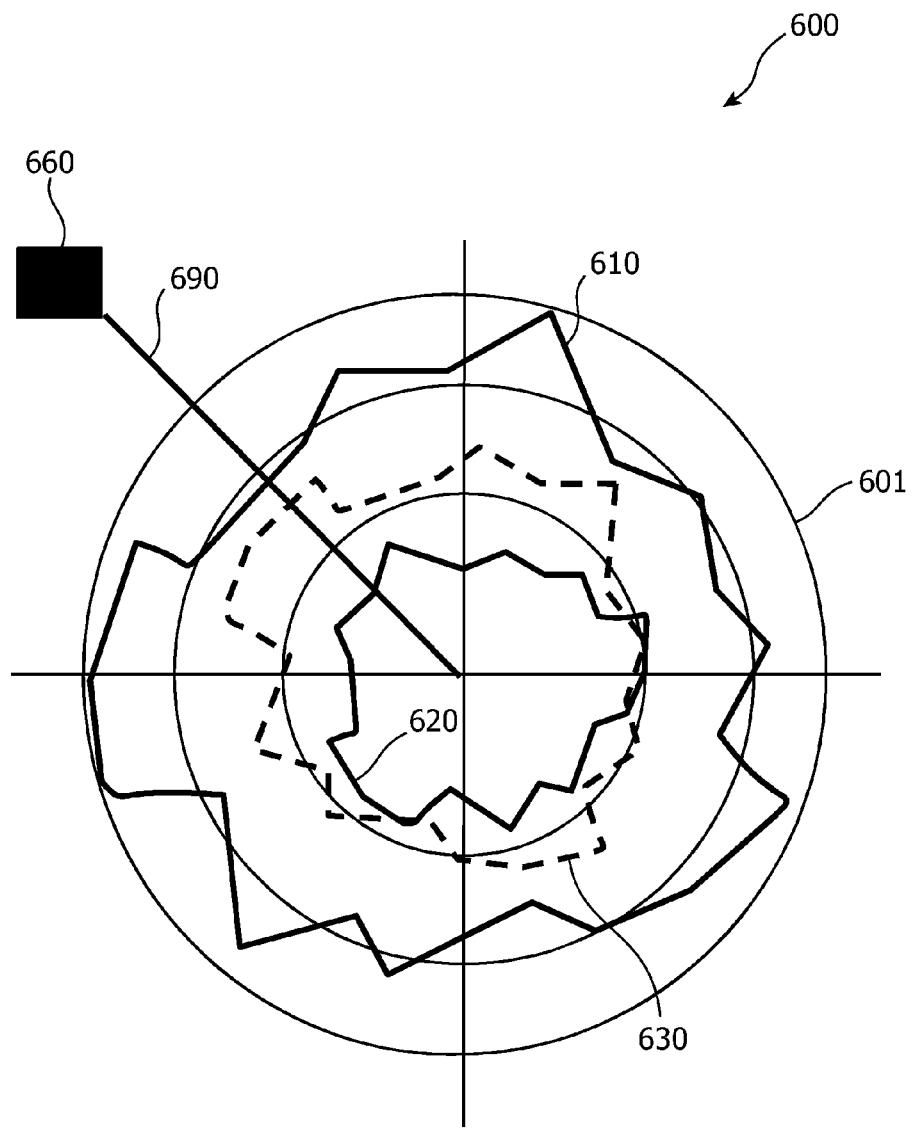
FIG. 12 depicts a further example of a data representation.

FIG. 12 depicts a representation 600 similar to the one depicted in FIG. 9B, except that the first 630, second 610 and third 630 visualization parameters have been determined for a plurality of spot positions 560 around the intermediate layer 550, and the grid has been made circular to create a polar plot representation 600. The grid 601 may optionally be indicated, and where useful, may indicate a scale for the polar plot. The polar plot 600 also comprises an indicator 660, 690, so that the radial position of a selected spot of interest 560 may be indicated to the user, such as a small rectangle 660 linked by a bar 690 to the centre of the polar plot 600. This is particularly advantageous in cases where each parameter visualized can be referenced to the same scale, preferably having the same unit of measure.

For example, if perfusion in the myocardium is measured, the intensity for the epicardial layer may be used for the second visualization parameter 610 and the intensity for the endocardial layer may be used for the third visualization parameter 620.

Figure 13A:
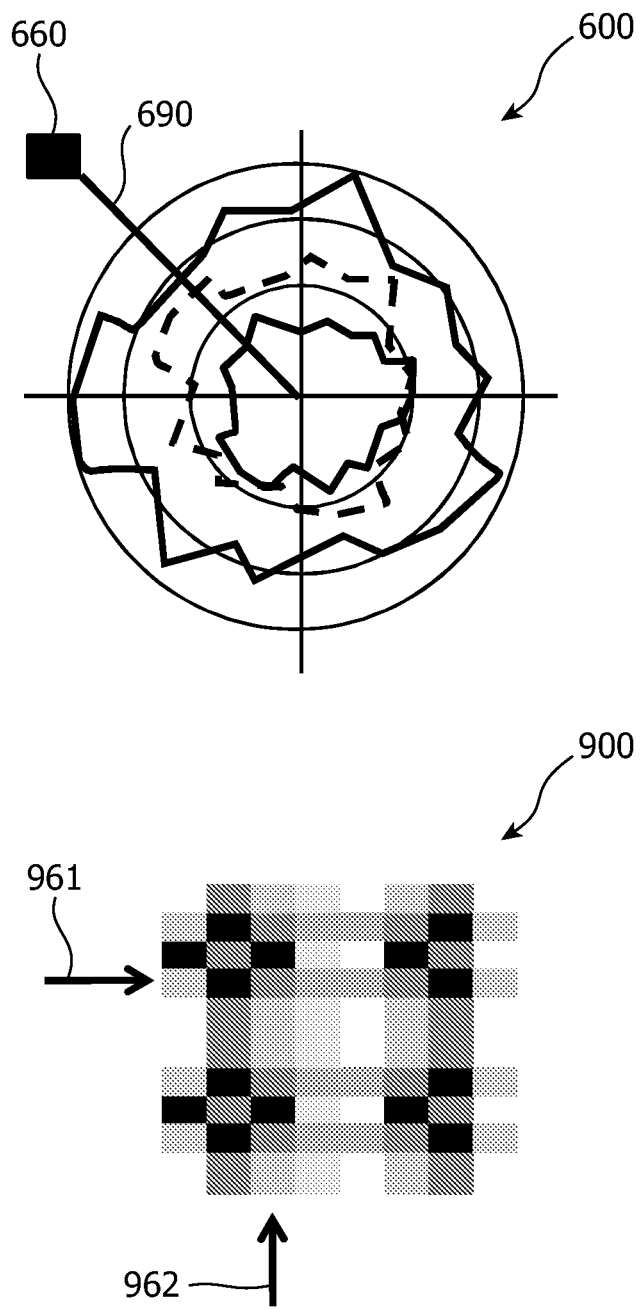
FIG. 13 depicts displays that may be presented to the user.

FIG. 13A depicts a display that may be presented to the user. The display comprises the polar plot 600 depicted in FIG. 12 and the 2D pixel array 900 of FIG. 11A. The 2D pixel representation 900 is provided with a temporal indicator 962, which indicates a selected time interval for which the second visualization parameter is determined. The 2D pixel representation 900 is also provided with a spatial indicator 961, which indicates a selected spot position. The polar plot 600 comprises an indicator 660, 690, which indicates the selected spot position 560.

Typically, the user is provided with a means to interact with the system, so that the user may influence what is displayed. The workstation 4 comprises input means 7 for the user to interact with the workstation 4, such as a keyboard, mouse, trackball, pointer, or drawing tablet. It may be advantageous to allow the user to change one or more of the settings associated with these indicators, using the input means 7.

If the user moves the temporal indicator 962 to select a different time interval, the 2D pixel array 900 remains the same. However, the first 630, second 610 and third 630 visualization parameters are determined again for a plurality of spot positions 560 around the intermediate layer 550 for the selected time interval. Therefore, the user will see the shape of the polar plots of the first 630, second 610 and third 630 visualization parameters change as the temporal indicator 962 is moved.

If the user moves the spatial indicator 961 to select a different selected spot position, the 2D pixel array 900 remains the same. Also the polar plots of the first 630, second 610 and third 630 visualization parameters remain the same. However, in the polar plot representation 600, the selected spot indicator 660, 690, is determined again. Therefore, the user will see the selected spot indicator 660, 690 move around the polar plot 600 as the spatial indicator 961 is moved. Conversely, if the user moves the selected spot indicator 660, 690 to select a different selected spot position, the user will see the spatial indicator 961 move to a different selected spot position.

By combining and linking the 2D pixel array 900 with the polar plot 600, the user is provided with an intuitive mean to visualize the visualization parameters, and to interpret the relationship between the time-series in the 2D pixel-array 900 and the associated quantitative analysis data in the polar plot 600. Additionally, as the number of time-series are increased due to a higher number of spot positions 560 around the intermediate layer 550, the user is only confronted with an increase in the density of the 2D-pixels 900—the relationship with the quantitative analysis data in the polar plot 600 remains clear due to the linked spatial position indicator 961 and the selected spot indicator 660, 690.

The skilled person will appreciate that the changes realized by the user interactions with any of the indicators is dependent on the role of the dimension represented by the indicator in the generation of the representation. For example, if perfusion in the myocardium is measured, some measure of the intensity, such as the average or mean, over a plurality of time intervals may be determined for the epicardial layer and may be used for the second visualization parameter 610. Similarly some measure of intensity for the endocardial layer over a plurality of time intervals may be used for the third visualisation parameter 620. The first visualization parameter value 630 may also represent the same measure of intensity in the first volume 170, associated with the selected spot position 560, over a plurality of time intervals. In this case, if the user moves the temporal indicator 962 to select a different time interval, the 2D pixel array 900 remains the same, and the first 630, second 610 and third 630 visualization parameters remain the same. Therefore, the user will see no change in either the 2D pixel array representation 900 or the polar plot representation 600.

In a typical application, the user workstation 4 is provided with further analytical possibilities, such as upslope, deconvolution, Patlak and arithmetic and statistic operations such as average, mean, maximum, minimum etc. These may be selected by the user to further analyze the parameter values in the first and second volume associated with the currently selected spot position. The results of this analysis may be displayed in an analysis window 5, as shown in FIG. 16, as simple figures or any suitable graphical representation.

Figure 13B:
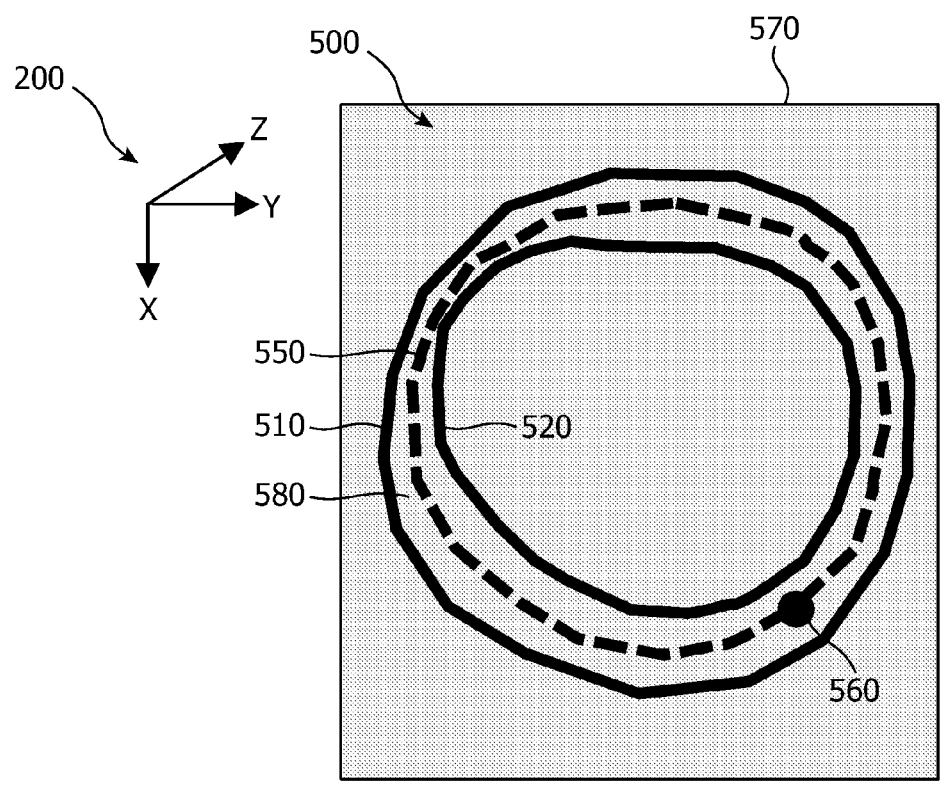
Figure 13B:
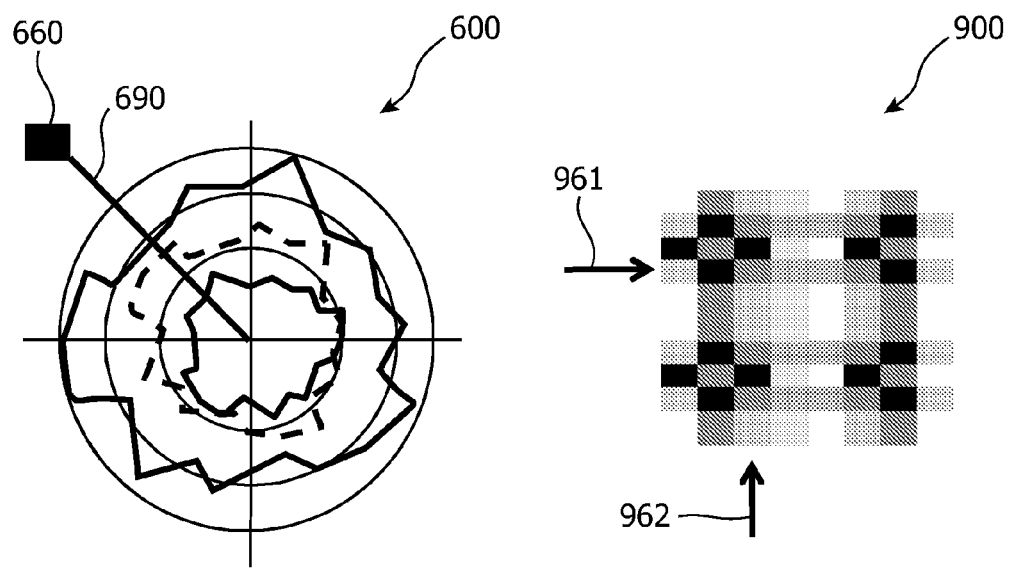

It may be advantageous to add a further representation 500 to complement the 2D pixel array 500 and the polar plot 600, as depicted in FIG. 13B. The representation 500 comprises an anatomical gray value image 570 depicting an image slice in the XY plane 200, overlaid with an indication of the boundaries of the structure 500 as viewed along the Z axis, so that the XY plane 580 is closest to the user. In particular, the first boundary 510, the second boundary 520 and the intermediate layer 530 are overlaid over the associated positions of the biological structure 500. This provides the user with an indication of the relationship between the structure 500 for which the parameters are determined and the anatomical structure. It may also be advantageous to indicate the position of the selected spot 560 on the intermediate layer.

The example of the user interaction described in relation to FIG. 13A is slightly modified in FIG. 13B.

If the user moves the temporal indicator 962 to select a different time interval, the 2D pixel array 900 and the structure overlay 500 remain the same. The polar plot 600 changes as described in relation to FIG. 13A. The anatomical gray value image 570 changes to display the acquired data for the selected time interval.

If the user moves the spatial indicator 961 to select a different selected spot position, the 2D pixel array 900, the structure overlay 500 and the polar plot 600 remain the same. However, in the polar plot representation 600, the selected spot indicator 660, 690, is determined again. Therefore, the user will see the selected spot indicator 660, 690 move around the polar plot 600 as the spatial indicator 961 is moved. Similarly, in the structure overlay the selected spot 560 will move around the intermediate layer 530 as the spatial indicator 961 is moved. Conversely, if the user moves the selected spot 560 or the selected spot indicator 660, 690 to select a different selected spot position, the user will see the spatial indicator 961 move to a different selected spot position.

Interaction by the user with the workstation 5 may be improved by highlighting the corresponding angular position in the polar plot 600 when the user moves the mouse cursor in the 2D pixel array 900. Alternatively, the corresponding row of the 2D pixel may be highlighted if the user moves the mouse cursor in the polar plot.

If the user moves the intermediate layer 530 to a different position between the first boundary 510 and the second boundary 520, the positions within the first volume will change, and the first visualization parameter will be re-determined. This means that the user will see a change in the values represented by the 2D pixel array 900 corresponding with the shift in position of the intermediate layer 530 as represented in the structure overlay 500. As the skilled person will realize, the intermediate layer 530 may also be selected to coincide with inner boundary 510 and outer boundary 520.

It may be particularly intuitive for a user to provide a means of moving the intermediate layer 530 between the first boundary 510 and the second boundary 520, using the scroll-wheel typically found in a mouse, as part of the user interfacing means 7.

As the imaging data may be comprised of a plurality of XY plane slices, it may also be particularly intuitive for the user to be provided with a means of moving through the image stack in effect in the Z direction by using the scroll wheel.

These scroll wheel functions may be enabled when a cursor is positioned over a particular area, or a particular area of one of the representations, to increase the intuitive feeling of the interface.

It is envisioned that the representation 500 may also comprise anatomical markers, such as the positions of blood vessels or arches in blood vessels. This may be particularly advantageous in helping the user associate the representations and the data with actual anatomical positions. For example, in analyzing perfusion data for the myocardium, the positions and orientations of the coronary arteries are important as the source of oxygenated blood, so proximity to the arteries is a factor in accurately interpreting the results. Also markers for the right ventricular inflection points may be considered advantageous. Such spatial markers may also be indicated in the 2D pixel array 400, 900 and/or the polar plot 600 at the appropriate places.

Figure 14:
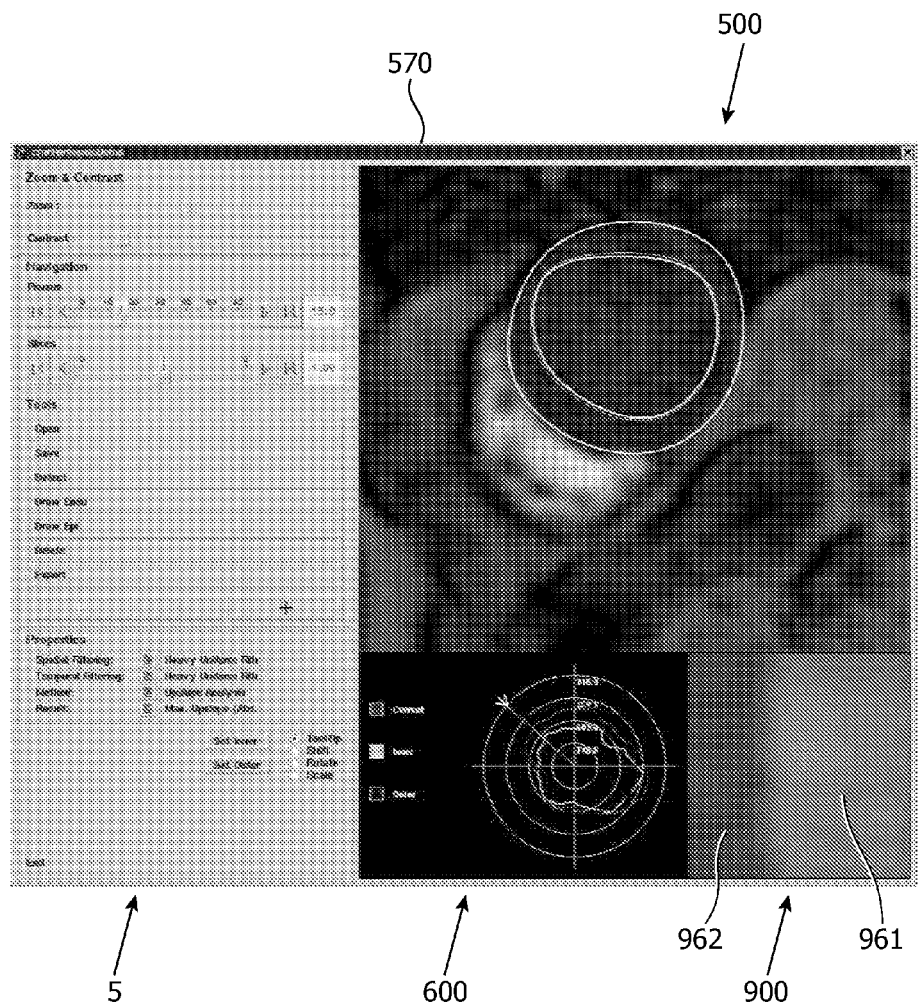
FIG. 14 shows a possible implementation of the representation combination of FIG. 13B.

FIG. 14 depicts a possible implementation of the representation combination of FIG. 13B. FIG. 14 shows a further representation 500 as depicted in FIG. 13B. The representation 500 comprises an anatomical gray value image 570 depicting an image slice in the XY plane, overlaid with an indication of the boundaries of the structure 500 as viewed along the Z axis, so that the XY plane is closest to the user. In particular, the first boundary, the second boundary and the intermediate layer are overlaid over the associated positions of the biological structure, in this case the myocardium. The representation 500 is complemented by the associated 2D pixel array 900 and the polar plot 600. The spatial indicator 961 and the temporal indicator 962 have been chosen to be lines overlaying the 2D pixel array 900. Optionally, an analysis window 5 may be provided to provide details on the analysis performed during the visualization of the imaging data, or to provide access to and results of additional analysis possibilities.

Additional indicators may be provided in any of the representations to indicate reference points currently selected or used in the analysis performed during the visualization of the imaging data, or selected or used during additional analysis.

By combining and linking the 2D pixel array 900 with the polar plot 600 and the structure overlay representation 500, the user is provided with an intuitive means to visualize the visualization parameters, which can be more easily related to the anatomical data. Additionally, as the number of time-series are increased due to a higher number of possible intermediate layer 550 positions, this increase is shielded from the user. The user is presented with far more analysis possibilities, without an increase in the complexity of the representations.

The possibility to visualize such a high resolution both along the intermediate layer 550 and between the first boundary 510 and the second boundary 520 means that very thin sections of tissue may be analysed. The biological structure 500 may therefore be an organ, a part of an organ, a lobe of an organ, a skeletal bone, a part of a skeletal bone, a muscle, a part of a muscle, a lymph node, part of a lymph node, a vessel, and part of a vessel. In addition, the biological structure may also be a tumor, primary tumor, metastatic tumor, cyst, pseudocyst, neoplasm, lymph node, lymphoma, fibroid, or nevus.

Figure 17:
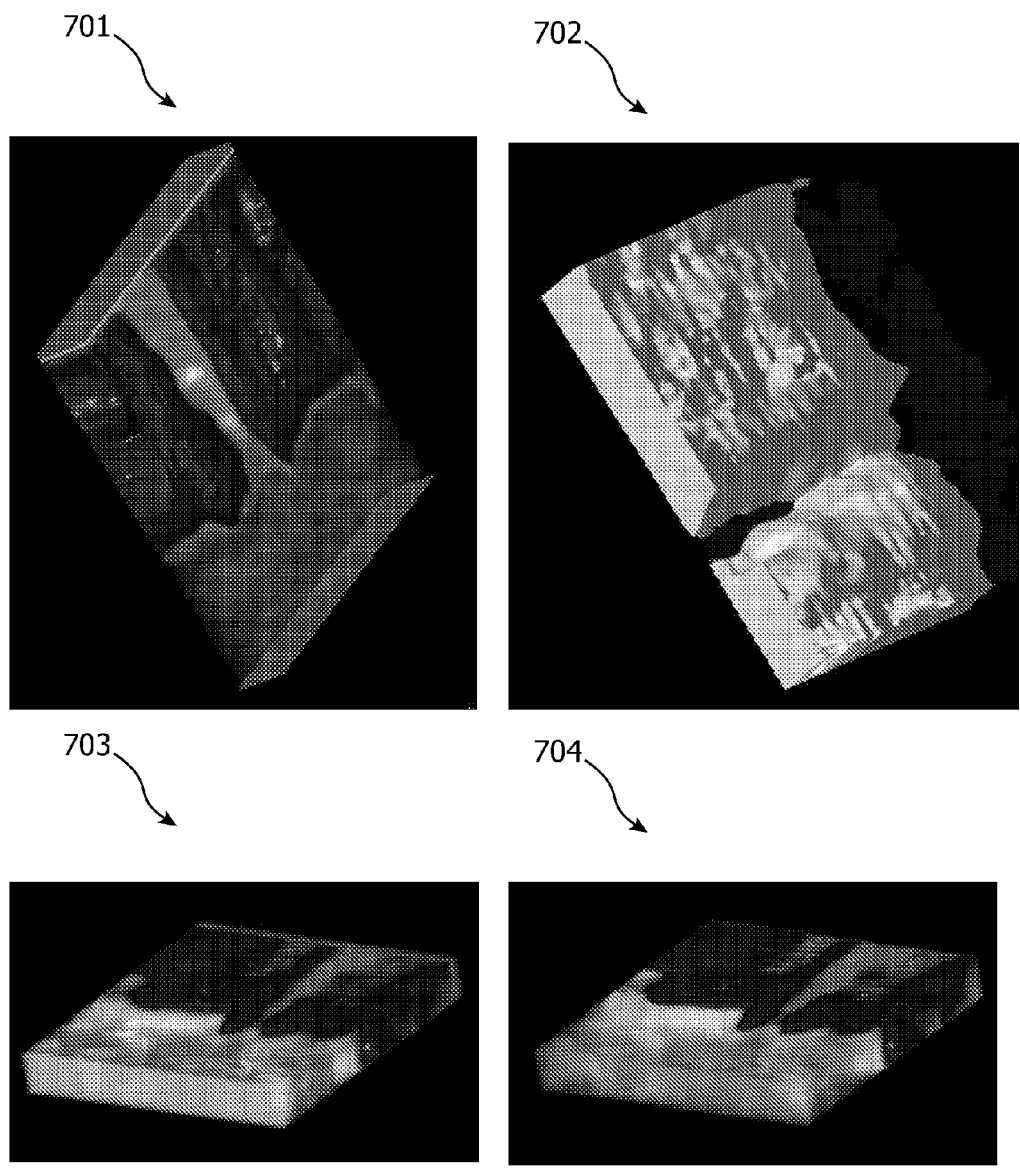
FIG. 17 depicts volumetric data representations.

The ability to visualize a higher degree of data density means that new types of representation become possible and particularly advantageous. FIG. 17 depicts alternative representations 701, 702, 703, 704 which may be described as volumetric representations.

For example, conventional volume rendering techniques may be used to visualize a time-variant parameter at a selected time interval at positions throughout a biological structure 100, such as that depicted in FIGS. 1 and 8, or structure 300 in FIG. 4. In the volumetric representation, the whole volume, or a selected portion of the whole volume, of a biological structure 100, 300 is visualized at the same time. By applying these conventional rendering techniques to a new type of volume, a powerful visualization tool has been provided.

Some of the possible types of volume rendering for a selected time interval are provided as examples in FIG. 17, one of which relates to a measure of perfusion in the myocardium between the epicardial and endocardial layers:

Representation 701 is a direct volume rendering, derived by mapping every sample value to opacity and a color. This is done with a "transfer function" which can be a simple ramp, a piecewise linear function or an arbitrary table. Once converted to an RGBA (red, green, blue, alpha) value, the composed RGBA result is projected on the correspondent pixel of the representation.

Representation 702 is an iso-surface rendering, wherein a surface is derived upon which all positions have the same measure of perfusion.

Representation 703 is a second direct volume rendering, displaying a different orientation and based on a different look-up table for colors and transparency.

Representation 704 is a third direct volume rendering, displaying a still further different orientation and based on yet another different look-up table for colors and transparency.

It may be advantageous to define various cut planes at various locations and/or orientations so that only a part of the volumetric representation 701, 702, 703, 704 is shown which corresponds to the intermediate layer 150 of FIG. 8.

Figure 15:
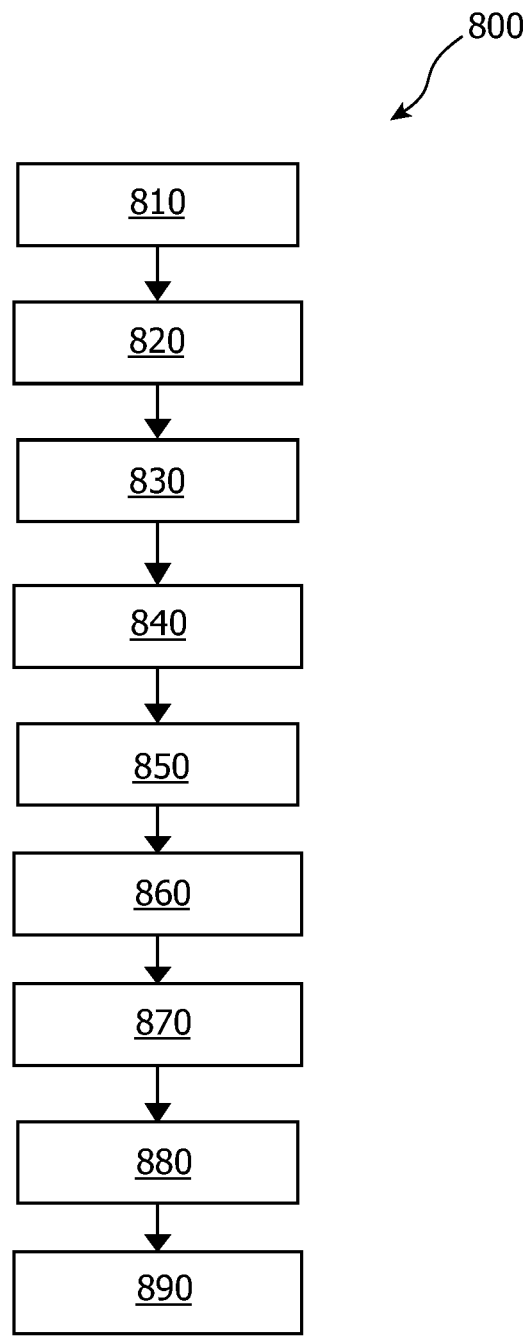
FIG. 15 depicts an example of a method of visualizing a time-variant parameter in a biological structure.

FIG. 15 depicts an example of a method 800 of visualizing a time-variant parameter in a biological structure. In particular, it is a method of visualizing perfusion in a human myocardium. The explanation of the method will focus on perfusion of the left ventricle. However, the method may also be used to visualize time-variant parameters in different layers of other parts of the heart (right ventricle and atria) or even other organs (kidney, prostate) that are imaged using first-pass enhancement MRI. Furthermore, the method is also applicable to time-variant parameters obtained from other imaging modalities (PET, SPECT, CT, etc.). The method 800 comprises the following parts:

Acquiring 810 the imaging data to be visualized. This may be performed by the system depicted in FIG. 16, if the system is capable of image acquisition using a suitable modality, or it may have been acquired at some earlier point in time by an independent image acquisition apparatus. It is also envisioned that the system may be comprised in an image acquisition apparatus.

Correcting 820 the imaging data for unwanted motion. For some imaging applications, it is important to remove certain time-dependent spatial variations, as these may affect the final visualization results, thereby creating artifacts. For example, when making images of the heart, a common problem is the patient's breathing motion that is present in the images. The first pass enhancement images may be registered to correct for the breathing motion that is present in the images. Appropriate registration techniques are known to the skilled person. Note that this correcting 820 is considered optional—such movement may also be prevented by asking the patients to hold their breath during image acquisition 810.

Delineating 830 the desired contours of the biological structure of interest. In other words, determining the positions corresponding to the extent of the biological structure. In this example, the left ventricular contours are delineated 830, either manually, semi-automatically or fully automatically.

Delineating 840 an intermediate layer within the biological structure. In other words, determining the positions corresponding to the intermediate layer. Delineating 830, 840 may be performed by any conventional means, such as interpolation or segmentation known in the art.

Sampling 850 the time-variant parameters, for example in the form of time-intensity curves, from the image data at positions along as well as across the myocardium. Optionally, these time-variant parameters may be filtered.

Analyzing 860 the time-variant parameters, using the desired and/or appropriate analysis technique. For example, upslope, deconvolution, and Patlak.

Visualising 870 the time-variant data as a perfusogram representation 900, 901 in combination with a polar plot 600 that shows associated quantitative analysis data as a result of the analysis 860. As the analysis of the time-variant data may be dependent on the position in the biological structure, the different plots 610, 620, 630 in the polar plot 600 relate to different myocardium layers.

It should be noted that the above-mentioned embodiments illustrate rather than limit the invention, and that those skilled in the art will be able to design many alternative embodiments without departing from the scope of the appended claims.

For example, any convenient visual means may be employed as an indicator 560, 961, 962, 660, 690, such as arrows, lines, blocks, dots, color coding etc. The indicators 560, 660, 690, 961, 961 may be arranged adjacent to the associated representation, or the indicators may be overlaid, on the associated representation, with visual aids such as highlighting, shading, boxes, lines and dashed lines. It is also envisioned that associated indicators and marks in the different representations will be given the same or a similar sort of indicator to illustrate the association, for example using the same colors.

Alternatively, the display may contain a plurality of one or more of the representations to increase the amount of data being visualized.

The skilled person, provided with the details of the methods disclosed, will be able to implement a computer program to carry out these methods when they are loaded and run on a computer.

In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer.

In the system claim enumerating a determination unit and a visualization display, several of these means may be embodied by one and the same item of hardware.

The mere fact that certain measures are recited in mutually different dependent claims does not indicate that a combination of these measures cannot be used to advantage.

The invention claimed is:

1. A system for visualizing a time-variant parameter at a plurality of positions in a biological structure, the system comprising:
   a determination unit implemented by a processer and configured to
   determine a value of the time-variant parameter at a plurality of positions in the biological structure, the structure extending in mutually perpendicular X, Y and Z directions;
   determine positions of a first and a second boundary extending in the Z direction, and positions of a first volume extending in Z disposed between the first and second boundaries;
   determine positions of a second volume generated by extending the first volume in the X-direction to both the first and the second XY boundary;
   determine a first visualization parameter for a plurality of time intervals from the time-variant parameters at a plurality of positions in the first volume;
   determine a second visualization parameter from the time-variant parameters at a plurality of positions in the second volume, and
   a visualization display configured to
   display a first representation showing the first visualization parameter at the plurality of time intervals, and
   display a second representation showing the first and second visualization parameters.

2. The system of claim 1, wherein the visualization display is further configured to display a third representation comprising an anatomical gray-value image comprising an XY section through the biological structure, overlaid with:
   the XY section of the first and the second boundary corresponding to the XY section through the structure, and
   the XY section through the first volume corresponding to the XY section through the structure.

3. The system of claim 2, wherein the system further comprises interactive means for a user to determine the XY section through the biological structure in the determination unit or visualization display.

4. A medical image acquisition apparatus comprising the system according to claim 2.

5. The system of claim 1, wherein the determination unit is further configured to determine the second visualization parameter from the time-variant parameters at a plurality of positions in the second volume at one of the plurality of time intervals.

6. The system of claim 1, wherein the determination unit is further configured to determine the second visualization parameter from the time-variant parameters at a plurality of positions in the second volume at the plurality of time intervals.

7. The system of claim 6, wherein the second visualization parameter is determined at a plurality of positions disposed on the first boundary and extending in the Z direction.

8. The system of claim 7, wherein the biological structure is the myocardium, the first boundary corresponds to the epicardial or endocardial layers of the myocardium, and the time-variant parameter is a measure of perfusion.

9. The system of claim 1, wherein the determination unit is further configured to determine a first visualization parameter for each of a plurality of first volumes, and the display unit is further configured to display the first representation showing the first visualization parameters for each of the plurality of first volumes at the plurality of time intervals.

10. The system of claim 1, wherein the determination unit is further configured to:
    determine a first visualization parameter for each of a plurality of first volumes, and
    determine a second visualization parameter for each of the plurality of second volumes associated with the plurality of first volumes;
    and the display unit is further configured to display the second representation showing the first and the second visualization parameter for each of the plurality of first volumes.

11. The system of claim 1, wherein the system further comprises interactive means for a user to determine a parameter in the determination unit or visualization display from the group consisting of:
    the positions of the first boundary, the positions of the second boundary, the positions of the first volume, the extent of the first volume in XY, the extent of the biological structure in Z, the plurality of time intervals, the first visualization parameter, the second visualization parameter, and any combination thereof.

12. A method of visualizing a time-variant parameter at a plurality of positions in a biological structure, comprising:
    determining, by a processor, a value of the time-variant parameter at a plurality of positions in the biological structure, the structure extending in mutually perpendicular X, Y and Z directions;
    determining positions of a first and a second boundary extending in the Z direction, and positions of a first volume extending in Z disposed between the first and the second boundary;
    determining positions of a second volume generated by extending the first volume in the X-direction to both the first and the second XY boundary;
    determining a first visualization parameter for a plurality of time intervals from the time-variant parameters at a plurality of positions in the first volume;
    determining a second visualization parameter from the time-variant parameters at a plurality of positions in the second volume, and
    displaying a first representation showing the first visualization parameter at the plurality of time intervals, and
    displaying a second representation showing the first and second visualization parameters.

13. The method of claim 12, wherein the method further comprises:
    displaying a third representation comprising an anatomical gray-value image comprising an XY section through the biological structure, overlaid with:
    the XY section of the first boundary and the second boundary corresponding to the XY section through the structure, and
    the XY section through the first volume corresponding to the XY section through the structure.

14. A computer program product, stored on a non-transitory computer readable medium, for carrying out the method of claim 12, when loaded and run on a computer.

* * * * *